US00PP16392P3

(12) United States Plant Patent

Ishihara et al.

(10) Patent No.: US PP16,392 P3
(45) Date of Patent: Mar. 28, 2006

(54) *PETUNIA* PLANT NAMED 'SUNCOPAHO'

(50) Latin Name: *Petunia hybrida*
Varietal Denomination: Suncopaho

(75) Inventors: Takuro Ishihara, Higashikurume (JP); Kazunari Iwaki, Omihachiman (JP); Kiyoshi Miyazaki, Hikone (JP); Shinya Miyano, Katori-gun (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 117 days.

(21) Appl. No.: 10/810,495

(22) Filed: Mar. 25, 2004

(65) Prior Publication Data

US 2005/0216998 P1 Sep. 29, 2005

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,768 | P | 6/1994 | Hirabayashi et al. |
| PP9,322 | P | 10/1995 | Tachibana et al. |
| 2003/0135906 | P1 | 7/2003 | Miyazaki et al. |

FOREIGN PATENT DOCUMENTS

| | | |
|---|---|---|
| JP | PBR 3463 | 3/1993 |
| JP | PBR 14307 | 3/2002 |

OTHER PUBLICATIONS

Explanation of Publications of Japanese PBR Registration or Application and family documents thereof.

Explanation for IDS Documents.

Suntory Ltd., "Flower & Green, the newest catalog 2002" Published 2001.

Jackson & Perkins Wholesale, Inc., USA, "The 2004 Suntory Collection" Published 2003.

Jackson & Perkins Wholesale, Inc., USA, "The 2003 Suntory Collection" Published 2002.

Pineae Greenhouses, Inc., USA, "Pineae Peak Performers featuring the 2004 Suntory Collection" Published 2003.

Moerheim New Plant bv., USA, "Suntory Collection 2004" Published 2003.

Ramm Botanicals Pty Ltd., AU., "Colour Wave Collection 2003–4 . . . beautiful flowering plants" Published 2002.

*Primary Examiner*—Kent Bell
(74) *Attorney, Agent, or Firm*—Christie, Parker & Hale, LLP

(57) ABSTRACT

Disclosed herein is a new and distinct variety of *Petunia* plant having a decumbent habit and short stems. The *Petunia* plant has abundant branching, and a great profusion of blooms, the whole plant remaining in bloom for a considerable period of time. The flowers are single and small, the petals having yellowish white color. The inside color of the corolla throat is light yellow green and the outside of the corolla tube is light yellow green. The plant exhibits high resistance to heat, cold and disease.

2 Drawing Sheets

Botanical/commerical classification: *Petunia hybrida/Petunia* Plant.

Varietal denomination: cv. 'Suncopaho'.

BACKGROUND OF THE VARIETY

The present invention relates to a new and distinct variety of *Petunia* plant, which originated from the crossing of a *Petunia* hybrid variety called '9Pt-27a' as the female parent and 'P59d-C10' as the male parent.

The *Petunia* is a very popular plant used for flower bedding and potting in the summer season. There are only a few *Petunia* varieties that do not have an upright growth habit and that have a high resistance to rain, heat, and diseases. *Petunias* of the 'Revolution' series include 'Revolution Purple pink' (U.S. Plant Pat. No. 6,915), 'Revolution Brilliant pink' (U.S. Plant Pat. No. 6,914), 'Revolution Brilliantpink-Mini' (U.S. Plant Pat. No. 6,899), and 'Revolution Blue vein' (U.S. Plant Pat. No. 9,322). These are decumbent type plants having long stems, a lower plant height, abundant branching, and a high resistance to heat, rain and disease. However, there are only a few *Petunia* varieties having a decumbent and compact plant shape, a great profusion of small size flowers, white petals and a high resistance to rain, heat, and disease. Accordingly, this invention was aimed at obtaining a new *Petunia* variety having white petals, together with the above features.

The female parent '9Pt-27a' (unpatented) used in the crossing of 'Suncopaho' is a strain of our breeding lines, having a spreading growth habit with many branches. It has medium size single flowers, the petals having a yellowish white color.

The male parent 'P59d-C10' (unpatented) used in the crossing of 'Suncopaho' is a strain of our breeding lines, having a decumbent growth habit with many branches. It has small single flowers, the petals having a yellowish white color.

In July 2000, crossing of '9Pt-27a' as the female parent and 'P59d-C10' as the pollen parent was conducted at Yokaichi-shi, Shiga-ken, Japan. In April 2001, 80 seedlings were obtained from that crossing. These seedlings were grown in pots in glasshouses and were evaluated. One seedling was selected in view of its growth habit, flower size and color in September 2001. That seedling was propagated by cutting and a trial was carried out by flower potting and bedding from April to September 2002 at Yokaichi-shi, Shiga-ken, Japan. The botanical characteristics of that plant were then examined, using similar varieties 'Revolution White' (U.S. Plant Pat. No. 8,768) and 'Sunchiffon' (U.S. Plant Pat. No. 15,024) for comparison. As a result, it was concluded that this *Petunia* plant is distinguishable from any other variety, whose existence is known to us, and is uniform and stable in its characteristics. The new variety of *Petunia* plant was named 'Suncopaho'.

In the following description, the color-coding is in accordance with the Horticultural Colour Chart of The Royal Horticultural Society, London, England (R.H.S. Colour Chart).

SUMMARY OF THE VARIETY

This new variety is unlike any *Petunia* commercially available as evidenced by the following unique combinations of characteristics.

1. Rather compact and decumbent growth habit with short stems.
2. Having abundant branching and a great profusion of blooms.
3. The flowers are single and small. The petal color is yellowish white (near R.H.S.158D).
4. The plant has a high resistance to cold, heat and disease.

The new variety 'Suncopaho' differs from the similar variety 'Revolution White' in the following points.

1. The spreading area of 'Suncopaho' is smaller than that of 'Revolution White'.
2. The stem of 'Suncopaho' is shorter and thinner than that of 'Revolution White'.
3. The internode length of 'Suncopaho' is shorter than that of 'Revolution White'.
4. The leaf of 'Suncopaho' is smaller and thinner than that of 'Revolution White'.
5. The flower size of 'Suncopaho' is smaller than that of 'Revolution White'.
6. The shape of petal of 'Suncopaho' is very broadly obovate, while that of 'Revolution white' is acute.

The new variety 'Suncopaho' differs from the similar variety 'Sunchiffon' in the following points.

1. The spreading area of 'Suncopaho' is smaller than that of 'Sunchiffon'.
2. The stem of 'Suncopaho' is shorter than that of 'Sunchiffon'.
3. The leaf of 'Suncopaho' is smaller and thinner than that of 'Sunchiffon'.
4. The petal color of 'Suncopaho' is yellowish white (near R.H.S.158D), while that of 'Sunchiffon' is moderate purplish pink (near R.H.S.68C).
5. The apex shape of petal of 'Suncopaho' is rounded, while that of 'Sunchiffon' is obtuse.
6. The petal lobation of 'Suncopaho' is deeper than that of 'Sunchiffon'.

The new variety of *Petunia* plant 'Suncopaho' was asexually reproduced by the use of cuttings at Yokaichi-shi, Shiga-ken, Japan, and the homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during July 2003 while cultivating under the trial field in 15 cm pots at an age of approximately 6 months at Yokaichi-shi, Shiga-ken, Japan.

DESCRIPTION OF THE VARIETY

Figure 1:
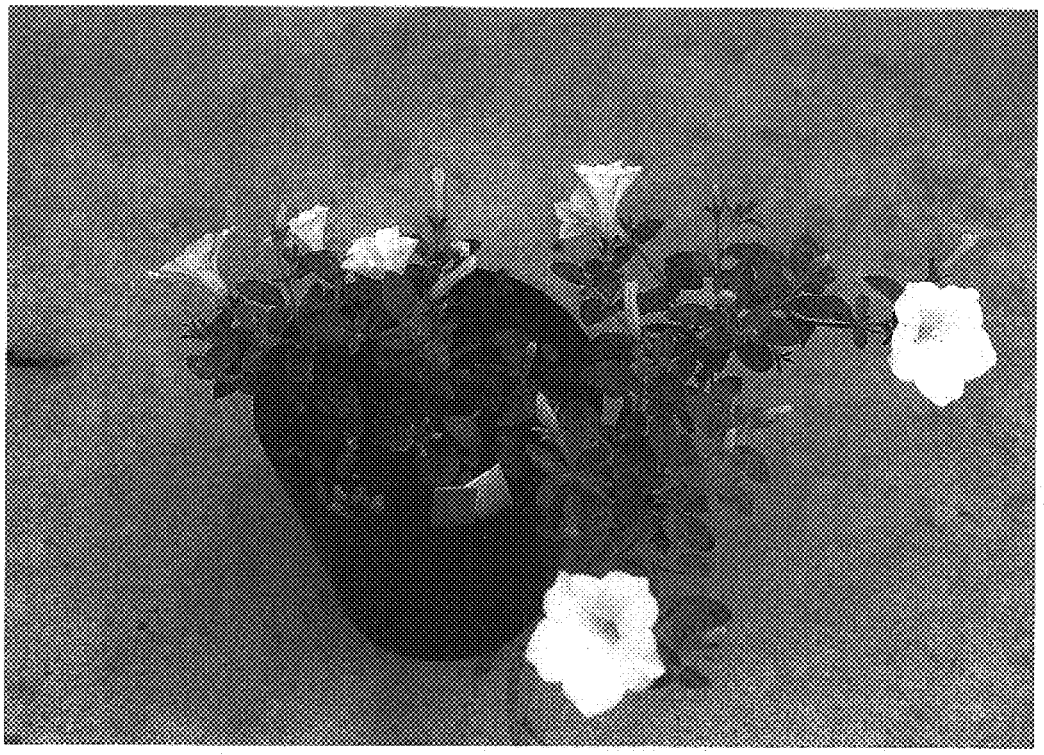
FIG. 1 is a photograph of a typical plant of the new variety of *Petunia* plant 'Suncopaho' while growing in a pot.
Figure 2:
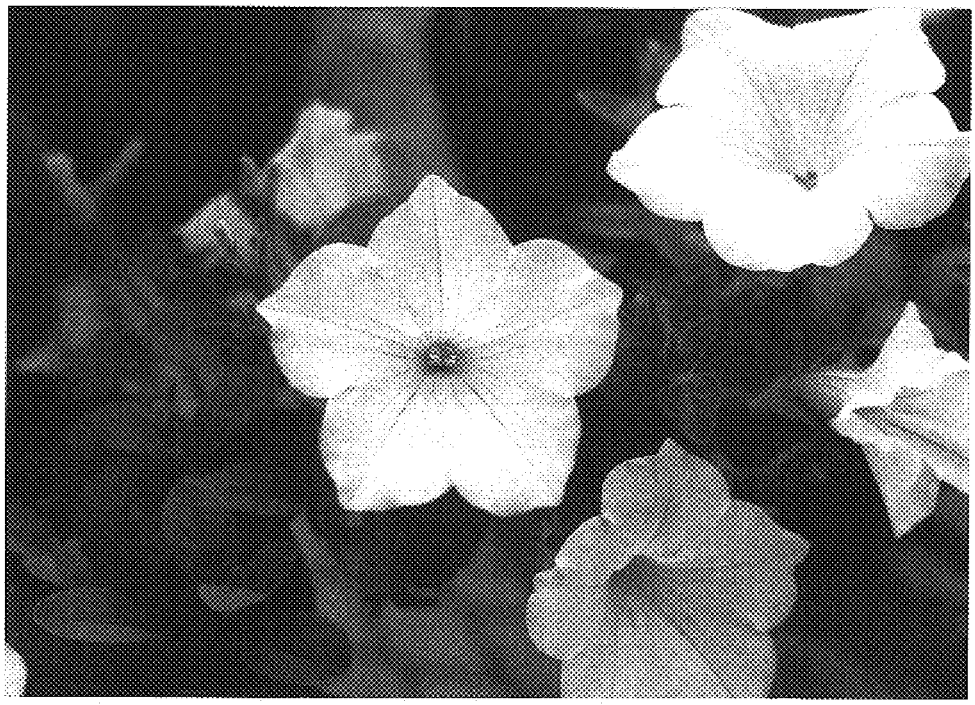
FIG. 2 is a photograph of a close view of flowers and leaves of the new variety of *Petunia* plant 'Suncopaho'.

The botanical characteristics of the new and distinct variety of *Petunia* plant named 'Suncopaho' are as follows when observed during July at Yokaichi-shi, Shiga-ken, Japan, at an age of approximately 6 months.

Plant:
- *Growth habit*.—Decumbent.
- *Plant height*.—Approximately 11.3 cm.
- *Spreading area of plant*.—Approximately 25.0 cm.
- *Blooming period*.—Early April to late October in the southern Kanto area, Japan. The plant shape does not change throughout this period. A typical flower commonly lasts approximately 5 days on the plant when experiencing a temperature of approximately 20° C.

Stem:
- *Length*.—Approximately 2.0 cm.
- *Thickness*.—Approximately 1.4 mm.
- *Pubescence*.—Sparse.
- *Branching*.—Abundant.
- *Internode length*.—Approximately 1.5 cm.
- *Color*.—Near R.H.S. 146B (moderate olive green).

Leaf:
- *Whole shape*.—Elliptic with entire margin. The apex shape is acute, and the base shape is attenuate.
- *Length*.—Approximately 3.2 cm.
- *Width*.—Approximately 1.9 cm.
- *Color*.—Upper side color is near R.H.S. 147A (moderate olive green). Lower side color is near R.H.S. 146A (moderate olive green).
- *Thickness*.—Approximately 0.1 mm.
- *Pubescence*.—Sparse.

Buds:
- *Shape*.—Cylindrical.
- *Length*.—Approximately 3.5 cm.
- *Diameter*.—Approximately 6.0 mm.
- *Color*.—Near R.H.S. 149C with venation near N144D.

Flower:
- *Petals*.—Width — Approximately 2.5 cm. Length from throat — Approximately 2.0 cm. Shape — Very broadly obovate. Margin — Entire. Texture — Smooth. Color — Lower surface — near R.H.S. 158D with venation near R.H.S. N144D.
- *Facing direction*.—Slanted upward.
- *Type*.—Single.
- *Shape*.—Funnel-shape, with five-fissures.
- *Shape of petal tip*.—Rounded.
- *Lobation*.—Medium.
- *Waviness of petal*.—Medium.
- *Diameter*.—Approximately 4.1 cm.
- *Depth*.—Approximately 4.0 cm.
- *Tube length*.—Approximately 2.3 cm,
- *Throat diameter, distal end*.—Approximately 1.0 cm.
- *Tube diameter, proximal end*.—Approximately 4.0 mm.

*Color*.—Near R.H.S.158D (yellowish white). Inside color of the corolla throat; Near R.H.S. 154C (light yellow green). Outside color of the corolla tube; Near R.H.S. 154C (light yellow green).

*Reproductive organs*.—1 normal pistil and 5 normal stamens. Color of pistil is near R.H.S. 154C (light yellow green). Color of stamen is near R.H.S. 144D (light yellow green).

Peduncle:

*Length*.—Approximately 7.0 mm.

*Diameter*.—Approximately 1.0 mm.

*Color*.—Near R.H.S. 144A.

*Surface*.—Pubescent.

Sepals:

*Shape*.—Narrow elliptic.

*Apex shape*.—Rounded.

*Base*.—Fused.

*Margin*.—Entire.

*Surface*.—Pubescent.

*Length*.—Approximately 0.8 cm.

*Width*.—Approximately 2.0 mm.

*Color*.—Upper surface — near R.H.S. 146B, lower surface — near R.H.S. 146B.

*Calyx*.—Narrow. 5 sepals fused at the base.

*Physiological and ecological characteristics*.—High resistance to cold, heat and disease. Moderate resistance to rain and pests.

This new variety of *Petunia* plant is most suitable for flower bedding and potting, particularly in hanging pots or planters. Pinching of old blossoms will enhance the formation of new blossoms.

It is claimed:

1. A new and distinct variety of *Petunia* plant named 'Suncopaho', substantially as herein illustrated and described.

* * * * *